United States Patent [19]

Lewicki

[11] Patent Number: 4,656,253

[45] Date of Patent: * Apr. 7, 1987

[54] MONOCLONAL ANTIBODIES AGAINST ALVEOLAR SURFACTANT PROTEIN

[75] Inventor: John Lewicki, Sunnyvale, Calif.

[73] Assignee: California Biotechnology, Inc., Mountain View, Calif.

[*] Notice: The portion of the term of this patent subsequent to Dec. 31, 2002 has been disclaimed.

[21] Appl. No.: 786,739

[22] Filed: Oct. 11, 1985

Related U.S. Application Data

[63] Continuation-in-part of Ser. No. 665,018, Oct. 26, 1984, Pat. No. 4,562,003.

[51] Int. Cl.$^4$ ............ A61K 39/395; C12N 5/00; C12P 21/00; C12Q 1/00
[52] U.S. Cl. ................... 530/387; 424/85; 435/7; 435/68; 435/70; 435/172.2; 435/240; 435/241; 435/810; 435/948; 435/172.3; 436/548; 436/808; 935/99; 935/100; 935/103; 935/104; 935/105; 935/110; 935/111; 530/350; 530/808; 530/809
[58] Field of Search ........... 260/112 R, 112 B, 111 R; 429/85; 435/68, 7, 70, 240, 241, 810, 172.3, 172.2, 948; 436/548, 808; 935/103, 104, 105, 99, 100, 110, 111; 530/350, 387, 808, 809

[56] References Cited

U.S. PATENT DOCUMENTS

| | | | |
|---|---|---|---|
| 4,364,934 | 12/1982 | Kung et al. | 424/85 |
| 4,364,936 | 12/1982 | Kung et al. | 424/85 |
| 4,427,653 | 1/1984 | Springer | 435/240 X |
| 4,469,630 | 9/1984 | Flashner | 260/112 B |
| 4,471,058 | 9/1984 | Smith et al. | 435/240 X |
| 4,472,500 | 9/1984 | Milstein et al. | 435/68 |
| 4,474,892 | 10/1984 | Murad et al. | 436/548 X |
| 4,486,530 | 12/1984 | David et al. | 435/7 |
| 4,517,289 | 5/1985 | Milford et al. | 260/112 R X |
| 4,562,003 | 12/1985 | Lewicki | 260/112 |

OTHER PUBLICATIONS

J. Immun. Meth. (1981), 42, 11–15, Uotila et al.
Nature, (1975), 256, 495–497, Kottler et al.
J. Biol. Chem. (1983), 258, 3509–3515, Lewicki et al.
Am. 3. Obstet. Gynecol., (Jan. 1984), 148, 48–53, Katyal et al.
American Review of Respiratory Disease (1974), 110, 273–281, King et al.

*Primary Examiner*—Howard E. Schain
*Attorney, Agent, or Firm*—Ciotti & Murashige

[57] ABSTRACT

Monoclonal antibodies specific for a protein associated with a lung surfactant complex, decreased levels of which are related to respiratory distress syndrome, are disclosed. The antibodies are useful for prediction and diagnosis of respiratory problems in newborns.

15 Claims, 6 Drawing Figures

Agglutination of DS-5 and DS-6 Latex particles by ASP

Fig. 5

FIG. 6

MONOCLONAL ANTIBODIES AGAINST ALVEOLAR SURFACTANT PROTEIN

CROSS-REFERENCE TO A RELATED APPLICATION

This application is a continuation-in-part of U.S. patent application Ser. No. 665,018, filed Oct. 26, 1984, now U.S. Pat. No. 4,562,003.

TECHNICAL FIELD

The invention relates to hybridoma technology and production of monoclonal antibodies using this technology. In more detail, the invention relates to hybridomas which produce monoclonal antibodies directed against alveolar surfactant protein.

BACKGROUND ART

Respiratory distress syndrome of the newborn (RDS) which is a leading cause of infant mortality and morbidity in the United States and elsewhere is associated, at least in part, with a deficiency in the level of a surfactant complex which normally is present at the air-fluid surface of the alveoli. The alveoli are small sacs in which gases are exchanged between blood and the air spaces of the lung, and the surfactant complex serves to reduce surface tension at this interface. If adequate levels of surfactant are not present, the alveoli will collapse during exhalation and cannot be reinflated by subsequent inhalations. The surfactant is a complex of an apo-protein (alveolar surfactant protein, "ASP") and phospholipids, principally depalmitylphosphocholine and phosphatidylglycerol, and is apparently stabilized by calcium ion.

Because appropriate levels of the surfactant complex are necessary for proper respiratory function, and because insufficient amounts of the complex are indicators of the presence of the syndrome, assay methods designed to detect the levels of components of this complex are important diagnostics of this syndrome. Because these components are present in the amniotic fluid, methods for their detection can be used in predicting the probability of incidence of this deficiency in premature and certain other infants associated with difficult or complicated pregnancies. This is made feasible by the fact that human fetal lung fluid exchanges freely with the external amniotic fluid; indeed, it has been estimated that 20-40% of the surfactant complex or its components are found in the amniotic fluid. The levels of the surfactant complex in the amniotic fluid are thus a good indicator of lung maturity and the risk of RDS developing at birth.

Presently existing diagnostic methods are, however, unsatisfactory. Assays of amniotic fluid (which can be withdrawn by amniocentesis) are based on measurement of the surfactant-specific phospholipids and the ability of the surfactant to stabilize bubbles at an air-water interface or other measures less closely related to the surfactant complex per se. See, e.g., U.S. Pat. No. 4,233,032 which discloses a surfactant test, and U.S. Pat. No. 4,071,770 which relies on fluorescence polarization. The most common phospholipid measurement is a lecithin/sphingomyelin ratio (L/S ratio), which may also be done in conjunction with determination of saturated phosphatidylcholine (SPC) (Torday, J., et al., *New England Journal of Medicine* (1979) 301:1013). Since there are other sources of phospholipids besides the surfactant complex, these assays are troubled by a relatively high number of false positives, especially in specimens contaminated with blood or meconium, or with specimens from complicated pregnancies such as those of diabetic mothers. Assays are commercially available which are based on measurement of the functional ability of surfactant to stabilize bubbles. For example, Beckmans' Lumadex FSI Fetal lung maturity test is one of these. False positives are a major problem with these assays as well.

Immunoassays of the ASP should offer inherently increased specificity and diminution of false positives. A relatively insensitive agglutination assay using polyclonal antiserum was used by King, R. J., et al., *J Appl Physiol* (1975) 39:735-741, but was never applied to clinical diagnosis. More sensitive radioimmunoassays have been developed to measure animal ASP, but have also been based on polyclonal antisera (King, R. J., et al, *American Review of Respiratory Disease* (1974) 110:273). The ELISA type assay disclosed by Katyal, S. L., et al., *Am J Obstet Gynecol* (1984) 148:48 also uses polyclonal antibodies prepared by injecting human or monkey lung washes into guinea pigs and rabbits. The inherent lack of affinity and specificity for ASP of polyclonal sera acts as a detriment to these assays.

The sensitivity and specificity of the assay would be greatly improved by the availability of homogeneous populations of antibodies directed against specific determinants of the ASP amino acid sequence. The present invention provides a source of such specific and homogeneous preparations.

DISCLOSURE OF THE INVENTION

Cells capable of producing reliable populations of homogeneous immunoglobulins directed against human ASP are provided. The invention takes advantage of the fusion of immortalizing cells to spleen cells derived from animals which were inoculated with purified preparations of the apoprotein associated with the surfactant complex.

In one aspect, the invention relates to monoclonal antibodies directed against human alveolar surfactant protein. In other aspects, the invention is directed to hybridoma cells capable of producing these antibodies, to methods of producing them, to methods of assaying levels of human ASP using these monoclonal antibodies, and to test kits capable of performing such analyses.

MODES OF CARRYING OUT THE INVENTION

A. Definitions

"Monoclonal antibodies (Mabs) specific for human ASP" refers to homogeneous populations of immunoglobulins which are capable of immunoreaction with these proteins. It is understood that there will be a number of antigenic determinants present on the surface of any protein, comprising among them several sequences of the peptide. The antibodies of the invention may be directed against one or more of these determinants. It has also been shown that more than one specific protein may be associated with the surfactant complex. Any characteristic protein associated with this complex may provide the requisite antigenic determinant.

Immunoglobulins, like all proteins, may exist in acidic, basic, or neutral form depending on their histories, and may be found in association with other molecules such as saccharides or lipids. The immunoglobulins of the present invention fall within the definition regardless of status in this regard as long as they remain capable of immunoprecipitation with human ASP.

"Cells" or "cell line" refers to the cells apparently denoted as well as to progeny thereof. It is known that during multiplication and growth, cells or cell lines may not remain precisely constant in their genetic makeup, and the progeny may, indeed, be distinguishable in some way from the parent cells. However, so long as the cells referred to herein retain the characteristic of secretion capability for Mabs specific for human ASP, as above-defined, they are to be considered included in the definition.

"Immortalizing cell line" refers to a cell line which can perpetually (for practical purposes) be maintained in cell culture—i.e., for an indefinite number of transfers. It must also, when fused to an ordinary nontransformed cell line (which would ordinarily not survive for more than a few days or weeks as a unicellular culture), be able to confer on the fusion product its own immortal properties.

B. General Description

The availability of Mabs with specific reactivity against the desired protein target offers the possibility of highly efficacious diagnostic tests for human ASP.

The mode of preparing the Mabs of the invention is illustrated below with respect to a particular hybridoma cell line producing the desired immunoglobulin; however, similar techniques may be used to prepare alternative embodiments of the specific Mabs. Briefly, as illustrated below, a commonly employed process involves fusion, under appropriate conditions, of an immortalizing cell line with a B-lymphocyte which produces the desired antibody. The immortalizing cell line illustrated below is a murine myeloma line. However, other immortalizing cell lines could be used, and are well known in the art. They include lines which are of mammalian origin, including, besides murine, of rat, bovine, and human origin. They are generally tumor lines, or cells obtained by transforming a normal cell line with, for example, Epstein Barr virus. Any immortalizing line can be used to prepare the hybridomas of the invention.

Similarly, techniques for obtaining the appropriate lymphocytes from mammals injected with the target antigen are well understood. Generally, either peripheral blood lymphocytes, if cells of human origin are desired, or spleen cells if mammalian, nonhuman sources can be used are employed. A subject mammal is injected with repeated dosages of the purified antigen, and the mammal is permitted to generate the desired antibody producing spleen cells or blood lymphocytes before these are harvested for fusion with the immortalizing line.

Techniques for fusion are also well known in the art, and in general, involve mixing the cells with a fusing agent such as, most commonly, polyethylene glycol. Preparation of hybridomas by fusing these two types of parents is by now well known in the art, and does not per se constitute part of the invention.

Successful hybridoma formation is assessed and selected by standard procedures such as, for example, HAT selection. From among successful hybridomas, those successfully secreting the desired antibody are screened by assaying the culture medium for their presence. Non-human as well as ASP can be used in immunoreaction based assays, including, without limitation, Western blot, ELISA, or RIA assays. The antibodies can be recovered from the medium using standard protein purification techniques.

The monoclonal antibody preparations can then be used to assay for the presence of human ASP in biological samples using a variety of assay systems similar to those suggested above for detection of antibody in the culture medium. A vast literature now exists with respect to various modifications of the basic assay principle, which is simply that there must be a specific association between target analyte and antibody which association is detectable qualitatively and/or quantitatively. Fluorescent or radioactive labels are generally used. One typical arrangement utilizes competition, between labeled antigen (e.g., ASP) and the analyte, for the same antibody, followed by physical separation of bound and unbound fractions. Analyte competes for the binding of the labeled antigen; hence more label will remain in the unbound fraction when larger amounts of analyte are present. Other embodiments of this basic principle include use of labeled antibodies per se, sandwich assays involving a three-way complex between analyte, anti-analyte antibody, and anti-antibody antibody wherein one of the components contains a label, and separation of bound and unbound fractions using an immunosorbent. Agglutination assays which result in visible precipitates are also available. Limet, et al, *J Clin Chem Clin Biochem* (1982) 20:142–147 (see below).

Two particularly preferred embodiments are a sandwich assay and an agglutination assay. In the preferred sandwich assay, the monoclonal antibody of the invention (e.g., DS-5) is immobilized on a support (Lewicki, J. A., et al, *J Biol Chem* (1983) 258:3509–3515). After incubation of the immobilized Mab with a standard or sample containing analyte, a second antibody, which is directed to a non-competing epitope on the antigen, or a polyclonal preparation is added. This second antibody may be labeled with $^{125}$I (IRSA) or an enzyme such as alkaline phosphatase, peroxidase, or $\beta$-galactosidase. The assay can also be amplified by using a third labeled antibody directed to the second, in this case unlabeled antibody. This assay is exemplified in ¶ C.7.

In the agglutination assay, the Mab is coated onto particles, such as latex particles or red blood cells and is incubated with standard or sample containing analyte in suitable micro-wells, and the degree of agglutination assessed by formation of a visible immunoprecipitate. This embodiment is set forth in detail in ¶ C.6 below.

The precise method of employing the monoclonal antibodies of the invention may be selected from among many, and the value and contribution of the invention lies in providing the specificity and increased affinity and reproducibility associated with these monoclonal antibody preparations.

Kits can also be assembled containing the reagents for assay. Depending on the precise procedure used, the kit may contain an immunosorbent, an anti-Mab antibody, systems for labeling such as radioactive materials or fluorescent materials, as well as suitable containers and supplementary reagents such as buffers. For example, in the case of an agglutination assay, a kit could contain (a) monoclonal antibody coated latex particles; (b) buffer; and (c) a suitable round-bottomed container to visualize the precipitate.

C. Example

The following illustration shows the method for preparing hybridomas which can serve as sources for the desired monoclonal antibodies, and of the antibodies thus produced. Also illustrated are procedures for diagnostic tests using the resulting antibodies, and an improved purification procedure for human ASP.

C.1. Preparation of Antigenic Canine ASP

Lungs from exsanguinated dogs were degassed and lavaged three times, with one liter of 5 mM Tris, 100 mM NaCl, pH 7.4 (Buffer A). The lung washings were spun at $150 \times g$ for 15 min to remove cellular debris and then at $20,000 \times g$ for 15 hr. The resulting pellet was dispersed in 1.64M sodium bromide, and the dispersion centrifuged at $100,000 \times g$ for 4 hr. The pellicle was resuspended in Buffer A and recentrifuged at $100,000 \times g$ for 1 hr, and the pellet, containing the surfactant complex, resuspended in water. The suspension was subsequently extracted in a 50 volume excess of n-butanol to remove lipids, stirred at room temperature for 1 hr, and the suspension was centrifuged at $10,000 \times g$ for 20 min. The precipitate was dried under nitrogen and washed with Buffer A, containing 20 mM octyl $\beta$-D-glucopyranoside. After centrifugation at $100,000 \times g$ for 1 hr, the pellet was dispersed in 0.3M lithium diiodosalicylate, 0.05M pyridine, pH 8.4, and diluted with an equal volume of $H_2O$. Lipids were further removed by extractions with 9 volumes of n-butanol. The final aqueous phase was lyophilized, resuspended in two ml Buffer A and a portion of the supension chromatographed on an SDS-polyacrylamide gel. The gel revealed three major protein components at 36,000 daltons, 32,000 daltons and 29,000 daltons, all of which appear to be components of the lung surfactant apoprotein.

C.2. Preparation of the Ig-Producing Fusion Partner

Eight week old Balb/c mice were immunized with 60 $\mu$g of the purified canine ASP preparation (i.e., the Buffer A suspension above), subcutaneously and intraperitoneally. Six weeks later, the mice were boosted with 20 $\mu$g ASP on three successive days. Forty-eight hr after the final boost, the mice were sacrificed and spleens removed. The spleens were placed in a $Ca^{2+}$ and serum free medium (CSF) described by Schneiderman, S., et al, *Somatic Cell Genet* (USA) (1979) 5:263–269, dispersed with 19 gauge needles, and passed through nylon, e.g., Nitex mesh (Tetko, Elmsford, N.Y.) to give a single cell suspension. The suspension was centrifuged at $1000 \times g$ for 10 min (Beckman TJ-6), and the pellet washed three times in 30 ml CSF.

C.3. Fusion of Mouse Spleen Cells to Myeloma Cells

The method is a modification of Kohler, G., et al, *Nature* (1975) 256:495–497.

In a parallel manner, 100 ml of SP2/0 myeloma cells, grown at a density of $2 \times 10^5$ cells/ml were harvested by centrifugation at $1000 \times g$ for 10 min. The $2 \times 10^7$ total cell pellet was washed three times with 30 ml CSF and repelleted. Finally, the spleen cells from ¶ C.2 and SP2/0 myeloma cells were combined and pelleted by centrifugation. One ml of polyethylene glycol (PEG MW 1000, Koch-Light Laboratories, Haverhill, England) at a concentration of 37% v/v in CSF was added to the combined pellet over a 90 sec period with continual mixing to promote fusion. The PEG was subsequently diluted by the addition of 10 ml CSF and cells were repelleted and washed in CSF. The cell pellet containing hybridoma fusion products was resuspended in RPMI 1640 (GIBCO, Santa Clara, CA) containing 15% fetal calf serum, and 100 ml was dispersed randomly in 500 microtiter wells. Hybridoma fusion products were selected by adding hypoxanthine-aminopterin-thymidine medium (HAT) (Littlefield, *Science* (1964) 145:709). The cells were allowed to grow for several weeks and were re-fed every 48 hr. Using this type of protocol successful hybridoma cultures were obtained.

C.4. Screening of Hybridomas for Anti-ASP Antibodies

After the cultures reached a cell density that covered 75–100% of the microtiter well surface, media from the hybridomas were screened for the presence of anti-ASP antibody, using an immobilized plate binding assay (Kennett, R. H., McKearn, T., and Bechtol, K. B. eds, *Monoclonal Antibodies* (1980) Plenum Press, New York). One $\mu$g portions of canine ASP, prepared as described in ¶ C.1 were incubated in individual microtiter wells in 50 $\mu$M sodium bicarbonate, pH 8.3, to promote binding of the protein to the polystyrene surface. Following a three hr incubation, 20% gamma globulin-free horse serum was added to occupy nonspecific protein binding sites on the polystyrene surface. Media from wells containing hybridomas were added and the wells incubated for 2 hr to permit binding of specific anti-ASP antibodies. Specifically bound antibodies were detected with $^{125}$I-sheep anti-mouse IgG. A ratio of three-fold or greater over control binding was considered positive. Of 150 colonies screened initially, 11 were demonstrated to be positive. The 11 clones were plated at a density of one cell/well and rescreened after obtaining an appropriate density. Six of the 11 original subclones screened positive. The monoclonal nature of the colonies was confirmed, and the 6 antibody-producing clones designated DS-1, DS-2, DS-3, DS-4, DS-5 and DS-6.

C.5. Purification and Characterization of Anti-ASP Antibodies

The 6 hybridomas of ¶ C.4 were injected into pristane-treated (2,4,6,10-tetramethyl pentadecane; Aldrich Chemicals) Balb/c mice to produce antibody-rich ascites fluid. $5 \times 10^6$ cells were injected per mouse (Kennett, R. H., supra). After 7–14 days, the ascites fluid was harvested with a syringe and 19-gauge needle. The individual monoclonal antibodies were purified from each fluid by Protein-A Sepharose (Pharmacia) chromatography as described by Ey and Prowse, *Immunochemistry* (1978) 15:429–436.

Figure 1:
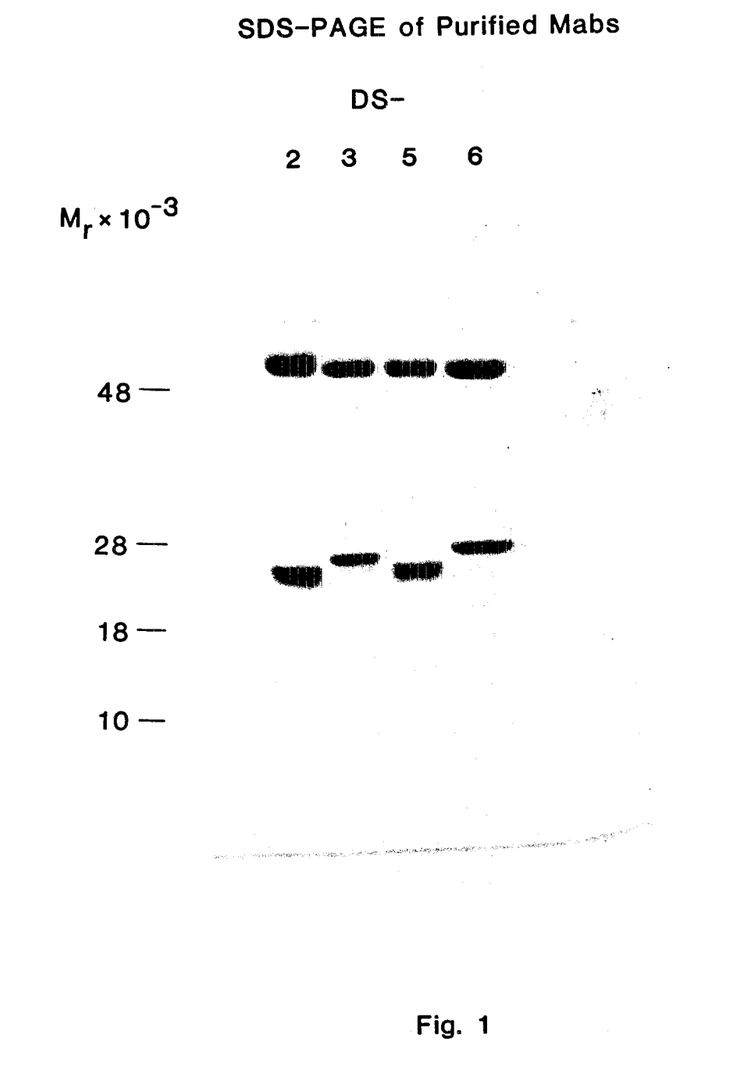
FIG. 1 shows the results of SDS-PAGE of Ig isolated from the hybridomas DS-2, DS-3, DS-5 and DS-6.

Four of the purified antibodies (from DS-2, DS-3, DS-5, and DS-6) were further characterized and shown to exhibit distinct heavy and light chains, with slight variations in electrophoretic mobility when subjected to SDS-PAGE as shown in FIG. 1. The single heavy and light chains are evidence for the monoclonal nature of each antibody. The antibodies were classified as IgG2a (from DS-2) or IgG1 (DS-3, DS-5 and DS-6) by their mobility on Protein A-Sepharose columns.

Figure 2:
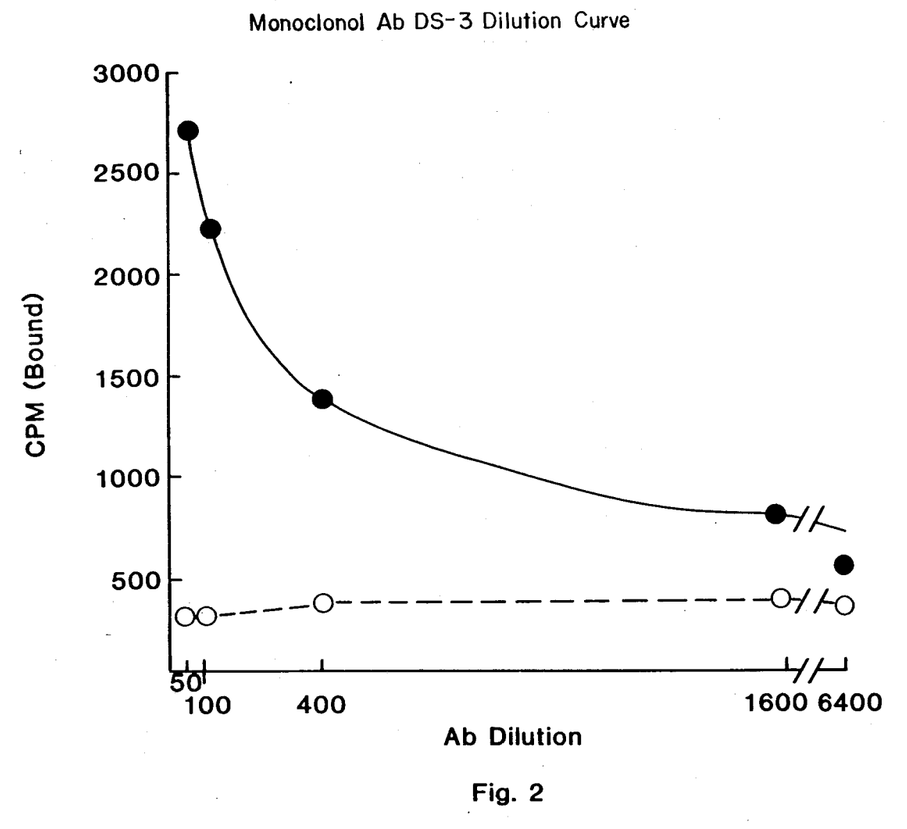
FIG. 2 shows the results of a binding experiment using dilutions of DS-3 monoclonal antibody (Mab) preparations.

Specificity of the purified Mabs was demonstrated as follows:

A. Mabs from all the hybridoma lines obtained and designated DS 1-6 as set forth in ¶ C.4 were shown to bind specifically to canine ASP immobilized on polystyrene microtiter wells, even at dilutions of 1:1600 and 1:6400. Antibodies were incubated with 1 μg of immobilized ASP. Specifically bound antibody was detected with $^{125}I$ labeled sheep anti-mouse IgG. FIG. 2 shows the results of a representative experiment using DS-3 Mab. The graph shows $^{125}I$ cpm bound to wells vs dilution of DS-3 Mab (solid line). A control monoclonal antibody prepared against an unrelated antigen did not bind to ASP at any dilution (dotted line).

Figure 3:
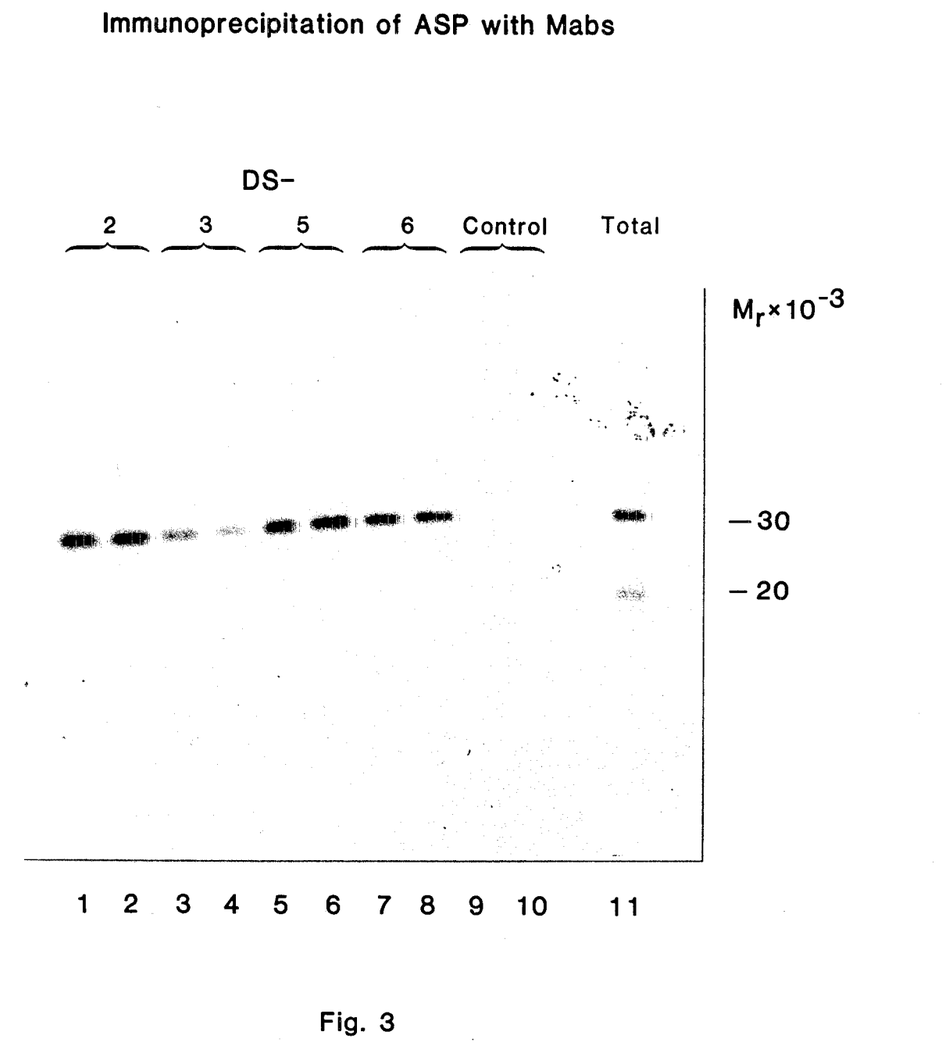
FIG. 3 shows the ability of DS-2, DS-3, DS-5 and DS-6 Mabs to precipitate selectively with $^{125}$I labeled ASP.

B. The Mabs were assayed for ability to immunoprecipitate canine ASP labeled with $^{125}I$ Iodobeads (Pierce Chemicals). FIG. 3 (lane 11) shows the results of a gel run on a labeled ($^{125}I$) ASP-containing sample before addition of Mab. The approximately 32 kD ASP is detected, along with a contaminating 20 kD protein. Lanes 1-10 show the results of gels run on immunoprecipitates prepared as follows: The sample was preincubated with Mab from one of DS-2, DS-3, DS-5 and DS-6, or control antibody. Following this preincubation, secondary rabbit anti-mouse IgG and Protein A-Sepharose were added to obtain an immunoprecipitation reaction. As shown in FIG. 3, all four monoclonal antibodies tested specifically immunoprecipitated the 32,000 dalton $^{125}I$ ASP (lanes 1-8). The contaminating 20,000 dalton $^{125}I$-labeled protein was not immunoprecipitated. Several control monoclonal antibodies (lanes 9 & 10) failed to immunoprecipitate the 32,000 dalton $^{125}I$-ASP.

Figure 4:
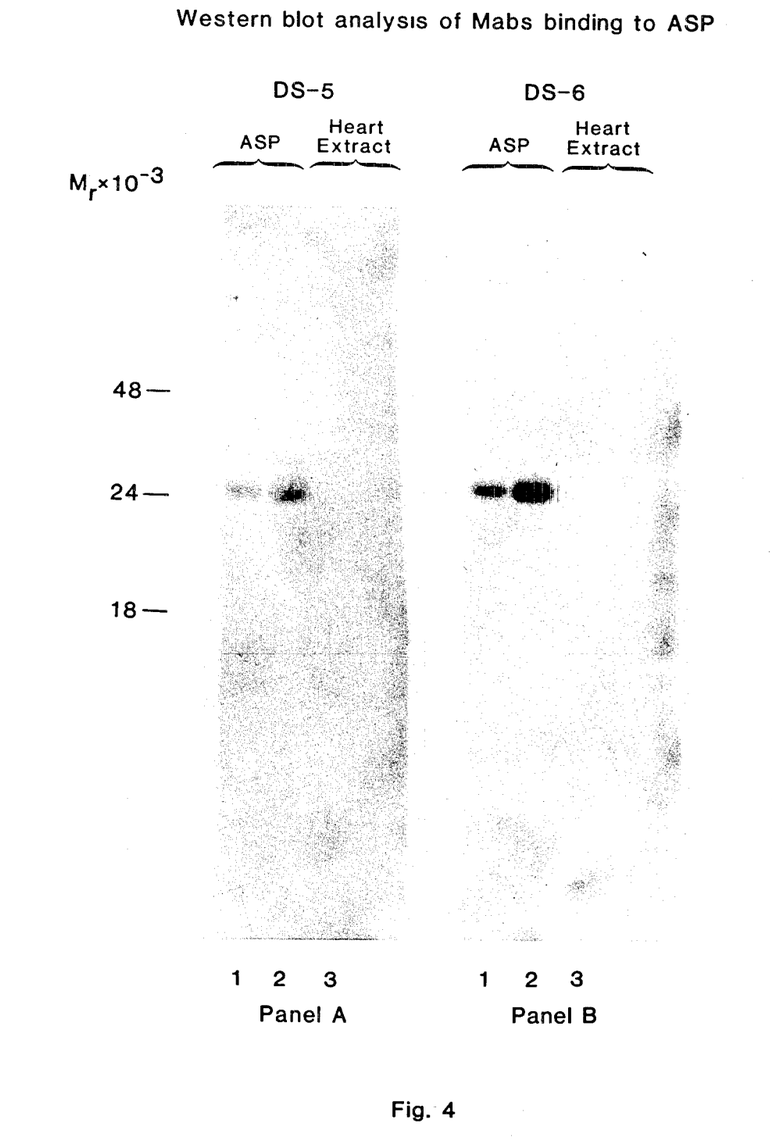
FIG. 4 shows representative Western blot analysis of the Mabs from DS-5 and DS-6 using ASP and non-ASP protein preparations.
Figure 5:
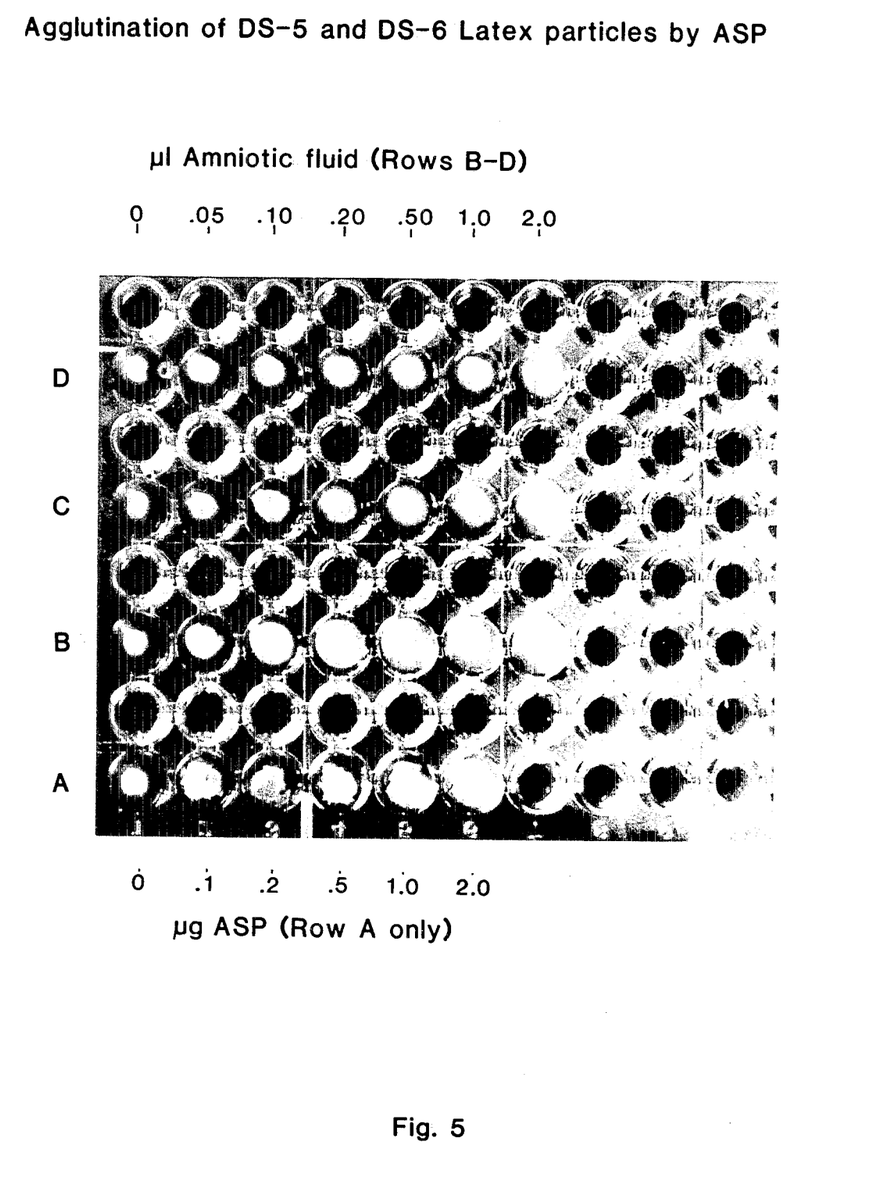
FIG. 5 shows the results of an agglutination assay for human ASP in amniotic fluid using Mabs from DS-5 and DS-6 both attached to latex particles.

C. Specificity was also confirmed by Western blot analysis of the antibodies (Towbin, H., *Proc NatlAcad Sci* (USA) (1979) 76: 4350-4354). A representative experiment using Mab from DS-5 and DS-6 is shown in FIG. 4 (Panels A and B, respectively). As shown in each panel, canine ASP was run in lanes 1 and 2 (1 μg and 3 μg, respectively) and a crude extract from rat heart containing many proteins was applied to lane 3. The results show that monoclonal antibodies from both DS-5 and DS-6 bound to the ASP (lanes 1 & 2) but not to the multiplicity of proteins derived from heart. Specifically bound antibody was detected with $^{125}I$-rabbit anti-mouse IgG.

C.6. Agglutination Assay

Antibodies prepared from DS-5 and DS-6 were attached to Latex particles, and the particles incubated with either increasing amounts of canine ASP (row A) or increasing amounts of amniotic fluid obtained from a full-term human pregnancy (row B). Increasing amounts of amniotic fluid obtained from partial term pregnancies, where there were also other indications of immature surfactant were also tested (rows C and D). Agglutination of the particles is clearly evident with greater or equal to 0.5 μg ASP (row A) or 0.2 μl of full-term amniotic fluid (row B). The amount of agglutination, however, is decreased in the presence of amniotic fluid from partial-term pregnancies as compared to full-term. In addition, the sample in row C was known to be highly contaminated with blood; the comparison with row D demonstrates that such contamination is likely not to interfere with the assay. Were the Mabs not specific for the ASP in the amniotic fluid, increased agglutination would have been expected in the presence of blood. The agglutination may also be measured spectophometrically at 360 nm. (Increase in agglutination results in a decrease in $A_{360}$.)

C.7. ELISA Assay

Ninety-six well microtiter plates were coated with monoclonal antibody secreted into the medium of DS-5 (1/300 dilution) or DS-1 (1/30 dilution) by incubating either at 37° C. for 90 min or at 4° C. for 18 hr, and washed four times with Buffer B. (Buffer B is phosphate-buffered saline containing 1% ovalbumin and 0.1% Tween-20.) 5-10 μl of human amniotic fluid or diluted purified human ASP standard were added to 90-95 μl Buffer B and the wells incubated with this mixture for 90 min at room temperature. The wells were again washed four times with Buffer B, and then treated with 100 μl of a 1/5000 dilution in Buffer B of rabbit anti-human ASP, prepared as described in ¶ C.8 below. After 90 min at room temperature, each well was again washed four times with Buffer B. Following this wash, 100 μl of a 1/3000 dilution in Buffer B of goat anti-rabbit IgG peroxidase conjugate (Cappel Laboratories) was added to each well, and the plates were incubated and washed as above.

The amount of antigen was determined by adding 200 μl of substrate (o-phenylenediamine plus $H_2O_2$ in phosphate buffer, pH 7) to each well for 30 min, and color reaction was terminated by the addition of 50 μl 4N sulfuric acid. Absorbance was read at 490 nm in an ELISA reader, giving the results shown in FIG. 6.

Figure 6:
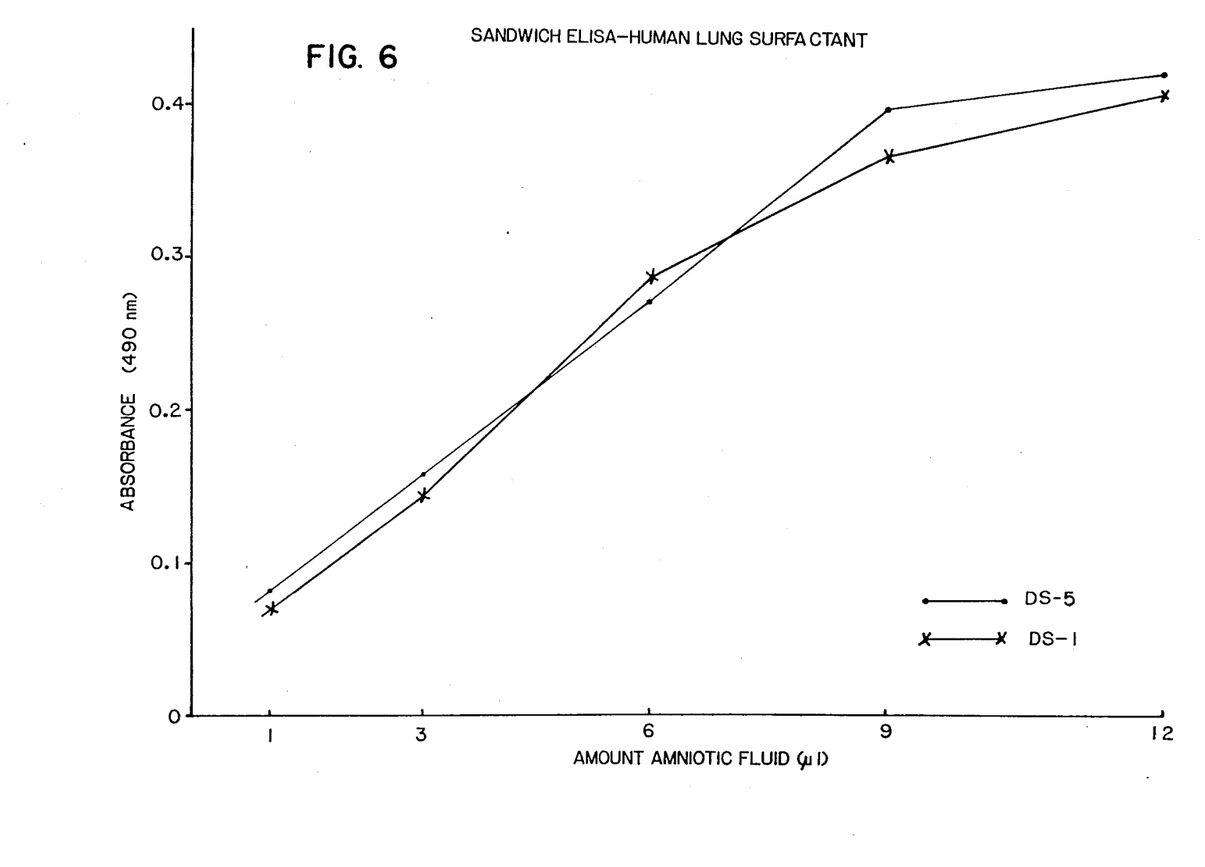
FIG. 6 shows the results of an ELISA assay for human ASP in amniotic fluid using Mabs from DS-5 and DS-1.

As shown in FIG. 6, DS-1 gives nearly linear results over a 12-fold concentration range; the results with DS-1 are similar, but at a higher dilution of Mab.

C.8. Preparation of Anti-Human ASP Polyclonal Sera

Immune sera were harvested from rabbits injected with purified human ASP prepared as described below. In general, the method involves repeated centrifugation at high speed to retrieve an ASP-containing pellet; extracting lipids from the pellet; and extracting impurities from the pellet.

Lung lavage from human patients diagnosed as having alveolar proteinosis was centrifuged at 20,000×g for 15 hr, and the resulting pellet resuspended in 0.1M NaCl. The suspension was centrifuged at 100,000×g for 1 hr, the pellet resuspended in 0.15M NaCl, and the resulting suspension centrifuged at 100,000×g for 1 hr. The resulting pellet was resuspended in water, and the aqueous suspension was extracted in a 50 volume excess of n-butanol at room temperature. The protein precipitate was removed from the butanol by centrifugation at 100,000×g for 20 min.

The resulting pellet was dried under nitrogen and extracted 2 times with 5 mM Tris, 100 mM NaCl, 20 mM octyl-β-D-glucopyranoside, pH 7.5, and the precipitate washed with 5 mM Tris, 100 mM NaCl. The precipitate was then extracted with (low salt) 5 mM Tris-HCl, pH 7.5, for 1 hr at room temperature to solubilize the ASP, and insoluble protein impurities were removed by centrifugation at 100,000×g for 1 hr.

The supernatant containsing human ASP was shown to be 90% homogeneous in material of an apparent molecular weight 32-36 kd (correct for human ASP) using SDS-PAGE.

Mixtures of the supernatant with Freunds Complete Adjuvant containing 250 μl of ASP protein were used to immunize rabbits; booster injections of this amount of ASP in admixture with Freunds Incomplete Adjuvant were given at 8 and 16 days after the initial injection. The sear were monitored and harvested at high titer of anti-human ASP.

On Oct. 25, 1984, Applicant has deposited with the American Type Culture Collection, Rockville, MD, USA (ATCC) the mouse hybridomas DS-3, ATCC accession no. HB-8651, DS-5, ATCC accession no. HB-8653, and DS-6, ATCC accession no. HB-8652. On Sept. 24, 1985 Applicant deposited with ATCC the mouse hybridoma DS-1, ATCC accession no. HB-8906. These deposits were made under conditions as provided under ATCC's agreement for Culture Deposit for Patent Purposes, which assures that this deposit will be made available to the US Commissioner of Patents and Trademarks pursuant to 35 USC 122 and 37 CFR 1.14, and will be made available to the public upon issue of a U.S. patent which requires this deposit to be maintained. Conversion to a deposit under the terms of the Budapest Treaty has been requested for these desposits. Availability of the deposited strain is not to be construed as a license to practice the invention in contravention of the rights granted under the authority of any government in accordance with its patent laws.

I claim:

1. A hybridoma specific against human alveolar surfactant protein (ASP) which is prepared by fusing an immortalizing cell line with spleen cells derived from a mammal immunized with purified non-human ASP and screened for anti-ASP activity against non-human ASP.

2. A method of producing monoclonal antibodies specific for human ASP which comprises culturing the hybridoma of claim 1 and recovering the Mab from the medium or injecting into a mouse the hybridoma of claim 1 and recovering the Mab from the malignant ascites or serum of the mouse.

3. Monoclonal antibodies (Mab) prepared by the method of claim 2.

4. A test kit for assessing the level of human ASP in a biological sample which comprises the Mab of claim 3.

5. A method for isolating human ASP which comprises fractionating lung fluid from human diagnosed as having alveolar proteinosis by the process which comprises
   (a) repeated centrifugation at high speed to retrieve an ASP-containing pellet;
   (b) extracting lipids from the pellet; and
   (c) extracting impurities from the pellet.

6. Human ASP prepared by the method of claim 5 which is approximately 90% homogeneous in material of an apparent molecular weight of 32–36 kd on SDS-PAGE.

7. The hybridoma DS-1 (ATCC HB8906).

8. Mab secreted by the hybridoma DS-1.

9. The method of detecting the presence of human ASP in a biological sample which method comprises:
   (a) immobilizing an Mab specific against human ASP on a solid phase support;
   (b) treating the sample with the immobilized Mab;
   (c) treating the mixture of (b) with a second antibody preparation specific for human ASP; and
   (d) detecting the presence of the second antibody preparation fixed to the solid support.

10. The method of claim 9 wherein the Mab is selected from DS-1 and DS-5.

11. The method of claim 9 wherein the second antibody preparation is a polyclonal preparation.

12. The method of claim 11 wherein the polyclonal antibody preparation was obtained by immunizing a mammal purified human ASP.

13. The method of claim 5 wherein the repeated centrifugation of (a) consists essentially of centrifuging at $20,000 \times g$ for 15 hours, resuspending the pellet, centrifuging at $100,000 \times g$ for one hour, resuspending the pellet, and centrifuging at $100,000 \times g$ for one hour.

14. The method of claim 13 wherein the extraction of lipids from the pellet of (b) consists essentially of extracting said pellet in a 50 volume excess of n-butanol at room temperature, followed by harvesting the pellet.

15. The method of claim 14 wherein the extraction of protein of (c) consists essentially of extracting said pellet in buffered detergent, wherein said detergent is octyl-$\beta$-D-glycopyranoside.

* * * * *